United States Patent
Krueger (10) Patent No.: US 7,201,722 B2
(45) Date of Patent: Apr. 10, 2007

(54) BONE BIOPSY INSTRUMENT HAVING IMPROVED SAMPLE RETENTION

(75) Inventor: John Krueger, Milwaukee, WI (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/280,166

(22) Filed: Oct. 25, 2002

(65) Prior Publication Data

US 2003/0050574 A1  Mar. 13, 2003

Related U.S. Application Data

(60) Continuation-in-part of application No. 09/799,143, filed on Mar. 5, 2001, now Pat. No. 6,730,043, which is a division of application No. 09/552,444, filed on Apr. 18, 2000, now Pat. No. 6,443,910.

(60) Provisional application No. 60/335,694, filed on Oct. 25, 2001.

(51) Int. Cl.
*A61B 10/00* (2006.01)
(52) U.S. Cl. ..................... 600/564
(58) Field of Classification Search ........ 600/562–570; 606/167–185; 604/22, 164.01
See application file for complete search history.

(56) References Cited

U.S. PATENT DOCUMENTS

| | | | |
|---|---|---|---|
| 2,219,605 A | 10/1940 | Turkel | |
| 2,827,039 A | 3/1958 | Seiger | |
| 3,007,471 A | 11/1961 | McClure, Jr. | |
| 3,175,554 A * | 3/1965 | Stewart | 600/567 |

(Continued)

FOREIGN PATENT DOCUMENTS

DE  4305226 A1  9/1993

(Continued)

OTHER PUBLICATIONS

Marketing literature entitled "Bone/Bone Marrow Biopsy Set with 'Extraction Cannula'", MD Tech.; Aug. 1998; 3 pgs.

(Continued)

*Primary Examiner*—Samuel G. Gilbert
(74) *Attorney, Agent, or Firm*—Andrew G. Rozycki (57) ABSTRACT

The invention disclosed herein relates to a sampling cannula for use in bone marrow biopsy procedures having structural features which facilitate sample retention within the device. In particular, the sampling cannula comprises an open trough-like portion, wherein the trough-like portion comprises at least one wall opening located proximal to the distal end in combination with an interior surface comprising a friction-enhancing surface texture adapted to facilitate sample retention. The invention further provides for a bone marrow biopsy system comprising an outer cannula having a sharpened distal tip, a sampling cannula having a distal trough portion in which the interior surface of the sampling cannula is exposed, at least one wall opening located within the trough portion located proximal to the distal tip of the sampling cannula, a friction-enhancing surface texture on at least a portion of the interior surface of the trough portion, wherein the sampling cannula is adapted to be inserted into an outer cannula and to sever a sample from the sampling site by rotational motion of the sampling cannula, and a stylet structured to be removably inserted into the outer cannula. The bone biopsy system can further include an ejector rod for expelling the retained sample from the sampling cannula.

14 Claims, 5 Drawing Sheets

U.S. PATENT DOCUMENTS

| | | | |
|---|---|---|---|
| 3,554,185 A * | 1/1971 | Kohl | 600/570 |
| 3,570,498 A | 3/1971 | Weighton | |
| 3,606,878 A | 9/1971 | Kellogg, Jr. | |
| 3,844,272 A * | 10/1974 | Banko | 600/566 |
| 3,882,849 A | 5/1975 | Jamshidi | |
| 3,929,123 A * | 12/1975 | Jamshidi | 600/567 |
| 3,995,619 A | 12/1976 | Glatzer | |
| 4,010,737 A | 3/1977 | Vilaghy et al. | |
| 4,013,080 A | 3/1977 | Froning | |
| 4,096,860 A | 6/1978 | McLaughlin | |
| 4,356,828 A | 11/1982 | Jamshidi | |
| 4,396,021 A | 8/1983 | Baumgartner | |
| 4,403,617 A | 9/1983 | Tretinyak | |
| 4,461,305 A | 7/1984 | Cibley | |
| 4,469,109 A | 9/1984 | Mehl | |
| 4,487,209 A | 12/1984 | Mehl | |
| 4,543,966 A | 10/1985 | Islam et al. | |
| 4,619,272 A | 10/1986 | Zambelli | |
| 4,630,616 A | 12/1986 | Tretinyak | |
| 4,643,196 A | 2/1987 | Tanaka et al. | |
| 4,649,918 A | 3/1987 | Pegg et al. | |
| 4,681,123 A | 7/1987 | Valtchev | |
| 4,682,606 A | 7/1987 | DeCaprio | |
| 4,699,154 A | 10/1987 | Lindgren | |
| 4,702,260 A | 10/1987 | Wang | |
| 4,708,147 A | 11/1987 | Haaga | |
| 4,747,414 A | 5/1988 | Brossel | |
| 4,766,907 A | 8/1988 | de Groot et al. | |
| 4,774,948 A | 10/1988 | Markham | |
| 4,781,202 A | 11/1988 | Janese | |
| 4,785,826 A | 11/1988 | Ward | |
| 4,790,329 A | 12/1988 | Simon | |
| 4,793,363 A | 12/1988 | Ausherman et al. | |
| 4,798,213 A | 1/1989 | Doppelt | |
| 4,799,494 A | 1/1989 | Wang | |
| 4,799,495 A | 1/1989 | Hawkins et al. | |
| 4,817,631 A | 4/1989 | Schnepp-Pesch et al. | |
| 4,838,282 A | 6/1989 | Strasser et al. | |
| D303,009 S | 8/1989 | Strasser et al. | |
| 4,873,991 A | 10/1989 | Skinner | |
| 4,903,709 A | 2/1990 | Skinner | |
| 4,922,602 A | 5/1990 | Mehl | |
| 4,931,059 A | 6/1990 | Markham | |
| 4,936,313 A | 6/1990 | Burkhardt et al. | |
| 4,953,558 A | 9/1990 | Akerfeldt | |
| 4,958,625 A | 9/1990 | Bates et al. | |
| 4,986,279 A | 1/1991 | O'Neill | |
| 5,012,818 A | 5/1991 | Joishy | |
| 5,027,827 A | 7/1991 | Cody et al. | |
| 5,031,634 A * | 7/1991 | Simon | 600/567 |
| 5,036,860 A | 8/1991 | Leigh et al. | |
| 5,040,542 A | 8/1991 | Gray | |
| 5,080,655 A | 1/1992 | Haaga | |
| 5,127,916 A | 7/1992 | Spencer et al. | |
| 5,172,701 A | 12/1992 | Leigh | |
| 5,284,156 A | 2/1994 | Schramm et al. | |
| 5,318,543 A | 6/1994 | Ross et al. | |
| 5,333,619 A | 8/1994 | Burgio | 128/754 |
| 5,341,816 A | 8/1994 | Allen | 128/754 |
| 5,348,022 A | 9/1994 | Leigh et al. | |
| 5,357,974 A | 10/1994 | Baldridge | |
| 5,368,045 A | 11/1994 | Clement et al. | |
| 5,385,151 A | 1/1995 | Scarfone et al. | |
| 5,394,887 A | 3/1995 | Haaga | |
| 5,429,138 A | 7/1995 | Jamshidi | |
| 5,449,001 A | 9/1995 | Terwilliger | |
| 5,462,062 A | 10/1995 | Rubinstein et al. | |
| 5,476,101 A | 12/1995 | Schramm et al. | |
| 5,476,102 A | 12/1995 | Como et al. | |
| 5,477,862 A | 12/1995 | Haaga | |
| 5,487,392 A | 1/1996 | Haaga | 123/753 |
| 5,507,298 A | 4/1996 | Schramm et al. | |
| 5,522,398 A | 6/1996 | Goldenberg et al. | |
| 5,526,821 A | 6/1996 | Jamshidi | |
| 5,595,186 A | 1/1997 | Rubinstein et al. | |
| 5,615,690 A | 4/1997 | Giurtino et al. | 128/754 |
| 5,634,473 A | 6/1997 | Goldenberg et al. | |
| 5,655,542 A | 8/1997 | Weilandt | |
| 5,713,368 A | 2/1998 | Leigh | |
| 5,718,237 A | 2/1998 | Haaga | 128/751 |
| 5,788,651 A | 8/1998 | Weilandt | |
| 5,807,277 A | 9/1998 | Swaim | |
| 5,823,970 A | 10/1998 | Terwilliger | 600/564 |
| 5,833,628 A | 11/1998 | Yuan et al. | |
| 5,843,001 A | 12/1998 | Goldenberg | |
| 5,868,684 A | 2/1999 | Akerfeldt et al. | |
| 5,885,226 A | 3/1999 | Rubinstein et al. | |
| 5,910,121 A | 6/1999 | Paolo et al. | |
| 5,944,673 A | 8/1999 | Gregoire et al. | 600/564 |
| 5,964,716 A | 10/1999 | Gregoire et al. | 600/564 |
| 6,007,496 A | 12/1999 | Brannon | |
| 6,063,037 A | 5/2000 | Mittermeier et al. | 600/567 |
| 6,066,153 A | 5/2000 | Lev | 606/180 |
| 6,086,543 A | 7/2000 | Anderson et al. | |
| 6,110,128 A | 8/2000 | Andelin et al. | 600/566 |
| 6,162,203 A | 12/2000 | Haaga | 604/272 |
| 6,165,136 A | 12/2000 | Nishtala | 600/564 |
| 6,241,687 B1 | 6/2001 | Voegele et al. | 600/566 |
| 6,416,484 B1 * | 7/2002 | Miller et al. | 600/564 |
| 6,428,487 B1 * | 8/2002 | Burdorff et al. | 600/568 |
| 6,764,452 B1 | 7/2004 | Gillespie et al. | |
| 2001/0005778 A1 | 6/2001 | Ouchi | 600/564 |
| 2002/0042581 A1 | 4/2002 | Cervi | 600/567 |
| 2002/0151822 A1 | 10/2002 | Burdorff et al. | 600/568 |
| 2004/0267268 A1 | 12/2004 | Gillespie et al. | |

FOREIGN PATENT DOCUMENTS

| | | |
|---|---|---|
| EP | 1136039 A2 | 9/2001 |
| EP | 1175866 A2 | 1/2002 |
| EP | 0738126 B1 | 4/2002 |
| FR | 2687303 A1 | 8/1993 |
| IT | 01261099 | 5/1996 |
| SU | 483978 | 9/1975 |
| SU | 567447 | 8/1977 |
| WO | WO 97/32524 | 9/1997 |
| WO | WO 00/10465 | 3/2000 |

OTHER PUBLICATIONS

Allegiance Corporation marketing literature entitled "Bone and Bone Marrow Biopsy Devices", Nov. 1995; 6 pgs.

* cited by examiner

BONE BIOPSY INSTRUMENT HAVING IMPROVED SAMPLE RETENTION

RELATED APPLICATION DATA

This application is based on U.S. Provisional Application No. 60/335,694 filed on Oct. 25, 2001 and is a continuation-in-part of U.S. patent application Ser. No. 09/799,143 filed Mar. 5, 2001, now U.S. Pat. No. 6,730,043 issued on May 4, 2004, which I a divisional of U.S. patent application Ser. No. 09/552,444 filed Apr. 18, 2000, now U.S. Pat. No. 6,443,910 issued Sep. 3, 2002.

FIELD OF THE INVENTION

The invention relates to the field of medical devices for use in biopsy procedures. In particular, the invention pertains to a bone marrow biopsy device and method for obtaining bone marrow samples therewith.

BACKGROUND OF THE INVENTION

Biopsy samples from bone tissue are typically collected from a sampling site in a patient by the use of bone biopsy devices. Typical bone biopsy devices include a hollow cannula which surrounds a stylet. The style includes a sharp distal tip which extends distally beyond the tip of the hollow cannula when the stylet is secured within the cannula. The combined cannula and stylet is used to penetrate through the cortex or outer layer of bone so as to sample the softer tissue or marrow within the bone. Once the cannula and stylet have penetrated into the bone, the stylet is removed and the cannula further advanced into the bone to capture a marrow sample.

The architecture of the tissue sample is important in several respects. Initially, the size of the sample is important, with larger sample sizes representing better samples for subsequent testing to be performed on the tissue. The larger the cannula and stylet which is used, however, the more pain is generated at the penetration site for the patient. Another aspect of sampling is minimizing damage to the sample, such as compressive forces, during sampling and removal.

A variety of bone biopsy devices have been proposed to improve the biopsy sampling procedure. Andelin et al. U.S. Pat. No. 6,110,128, Guirtino et al. U.S. Pat. No. 5,615,690 and Mittermeier et al. U.S. Pat. No. 6,063,037 describe a biopsy devices with structural features designed to enhance sample retention. Other bone biopsy devices have been developed which aid in the preservation of sample integrity by virtue of their structure. One such device is described in Krueger et al., U.S. Pat. No. 6, 443,910, which includes a sampling cannula having a "cutting finger" on the distal portion of the cannula.

Difficulty has been encountered in the art in the balancing between the structural requirements of bone biopsy devices and desirable sampling attributes. Providing bone biopsy devices that consistently sample without damaging forces being exerted upon the sample has proven challenging. Furthermore, accommodating patient comfort by reducing the need for multiple site sampling has presented another challenge. Preserving the architecture of the sample during its obtaining and removal presents yet another factor to be balanced in bone biopsy devices.

There is a need in the field of medical bone biopsy devices for biopsy devices which facilitate the retention of the obtained sample while at the same time preserving the structural integrity of the sample and reducing the amount of trauma to the patient.

SUMMARY OF THE INVENTION

The invention provides for a bone marrow biopsy device, specifically a sampling cannula, having structural features which improve the ability to sever and retain a relatively large marrow sample. It has been discovered that a sampling cannula can be constructed which affords the benefits of obtaining a relatively long core of bone tissue sample and enhancing the retention of the sample within the cannula while at the same time preserving the structural integrity of the sample. In particular, it has been discovered that a bone marrow sampling cannula having the advantages of an open trough-like distal structure can comprise both a friction-enhancing interior surface texture and wall openings which facilitate sample retention without substantially damaging the biological "architecture" of the core sample.

The invention provides for a sampling cannula for use in bone marrow biopsy system comprising:
  a sampling cannula having a distal trough portion in which the interior surface of said sampling cannula is exposed;
  at least one wall opening located within said trough portion located proximal to the distal tip of said sampling cannula;
  a friction-enhancing surface texture on at least a portion of the interior surface of said trough portion;
  wherein said device is adapted to be inserted into an outer cannula and to sever a sample from the sampling site by rotational motion of the sampling cannula.

In a preferred embodiment, the trough portion comprises a plurality of wall openings. In another preferred embodiment, each wall opening comprise a substantially rectangular shape.

The invention further provides for a bone marrow biopsy system comprising:
  an outer cannula having a sharpened distal tip;
  a sampling cannula having a distal trough portion in which the interior surface of said sampling cannula is exposed;
  at least one wall opening located within said trough portion located proximal to the distal tip of said sampling cannula;
  a friction-enhancing surface texture on at least a portion of the interior surface of said trough portion;
  wherein said device is adapted to be inserted into an outer cannula and to sever a sample from the sampling site by rotational motion of the sampling cannula; and
  a stylet structured to be removably inserted into the outer cannula.

In a preferred embodiment, the distal tip of the trough portion of the sampling cannula resides within the outer cannula such that the trough portion distal tip terminates proximal to the distal tip of the outer cannula. The bone marrow biopsy system can further comprise an ejector rod.

DETAILED DESCRIPTION OF THE DRAWINGS

As used herein, the terms "trough" and "trough-like" as used to describe a structural feature of the device of the invention, are meant to describe a cannula structure having an open segment at which the interior surface of the cannula is exposed through an elongated, generally linear open region on the opposite side from an intact portion.

The term "substantially rectangular" as used to refer to a wall opening of the sampling cannula is intended to encompass variations of length, width, and overall shape provided there is an overall longitudinal dimension of such opening.

Figure 1:
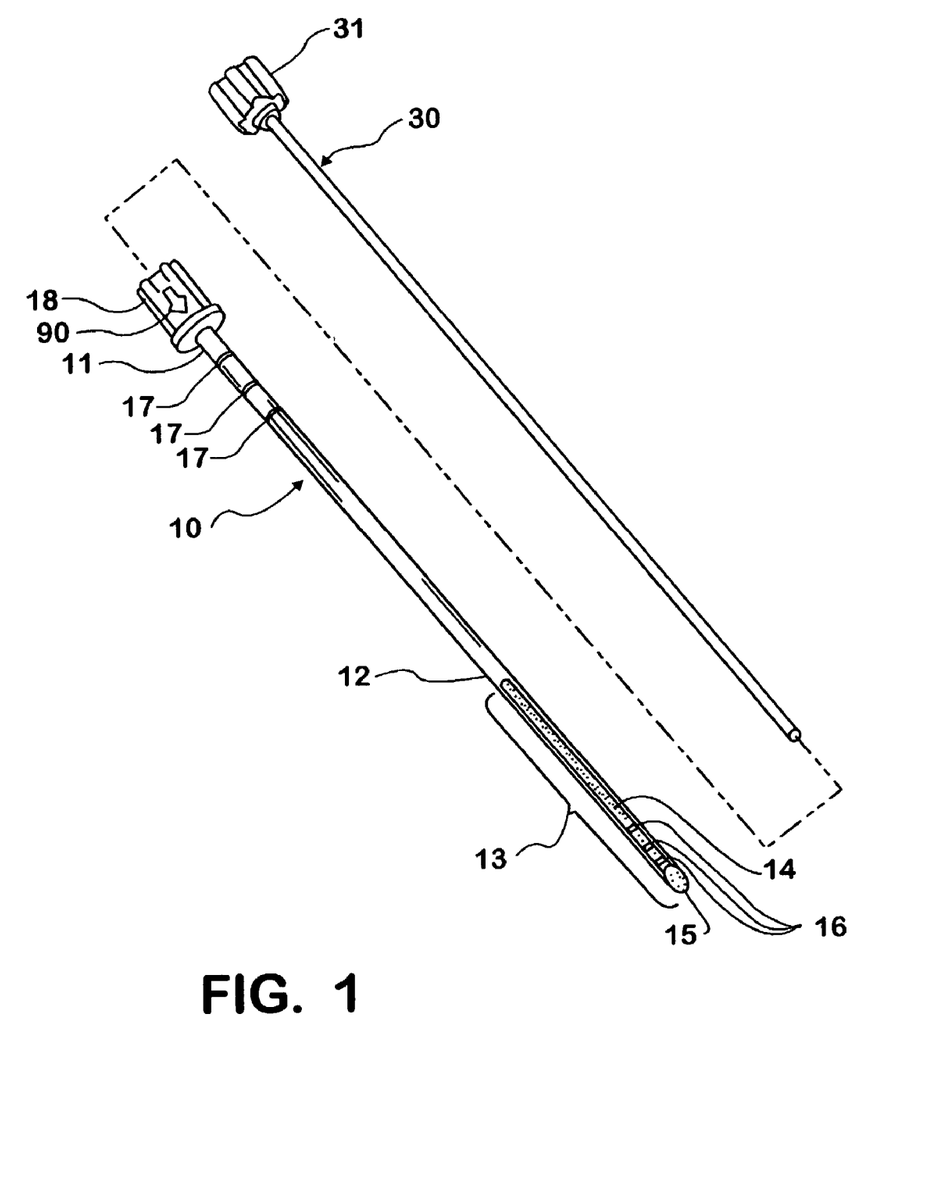
FIG. 1 is an overall perspective view of the sampling cannula and an ejector rod according to one embodiment of the invention.
Figure 2:
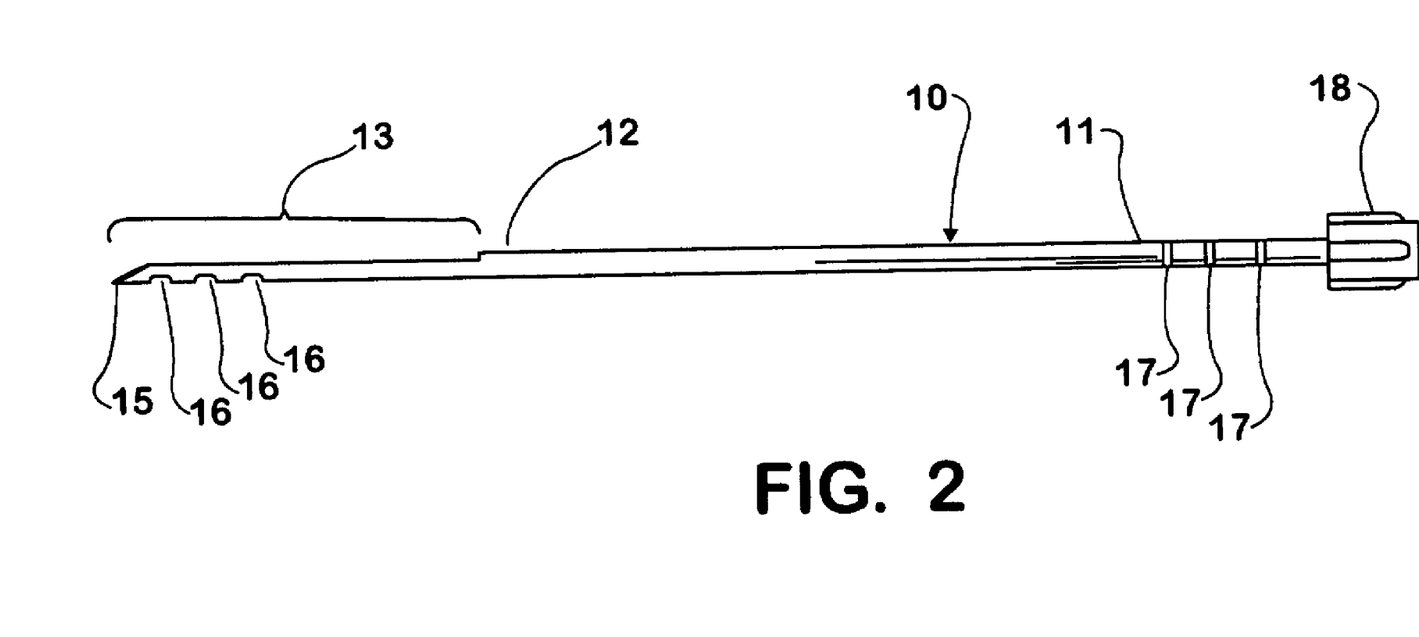
FIG. 2 is a side view of the sampling cannula according to one embodiment of the invention.
Figure 3:
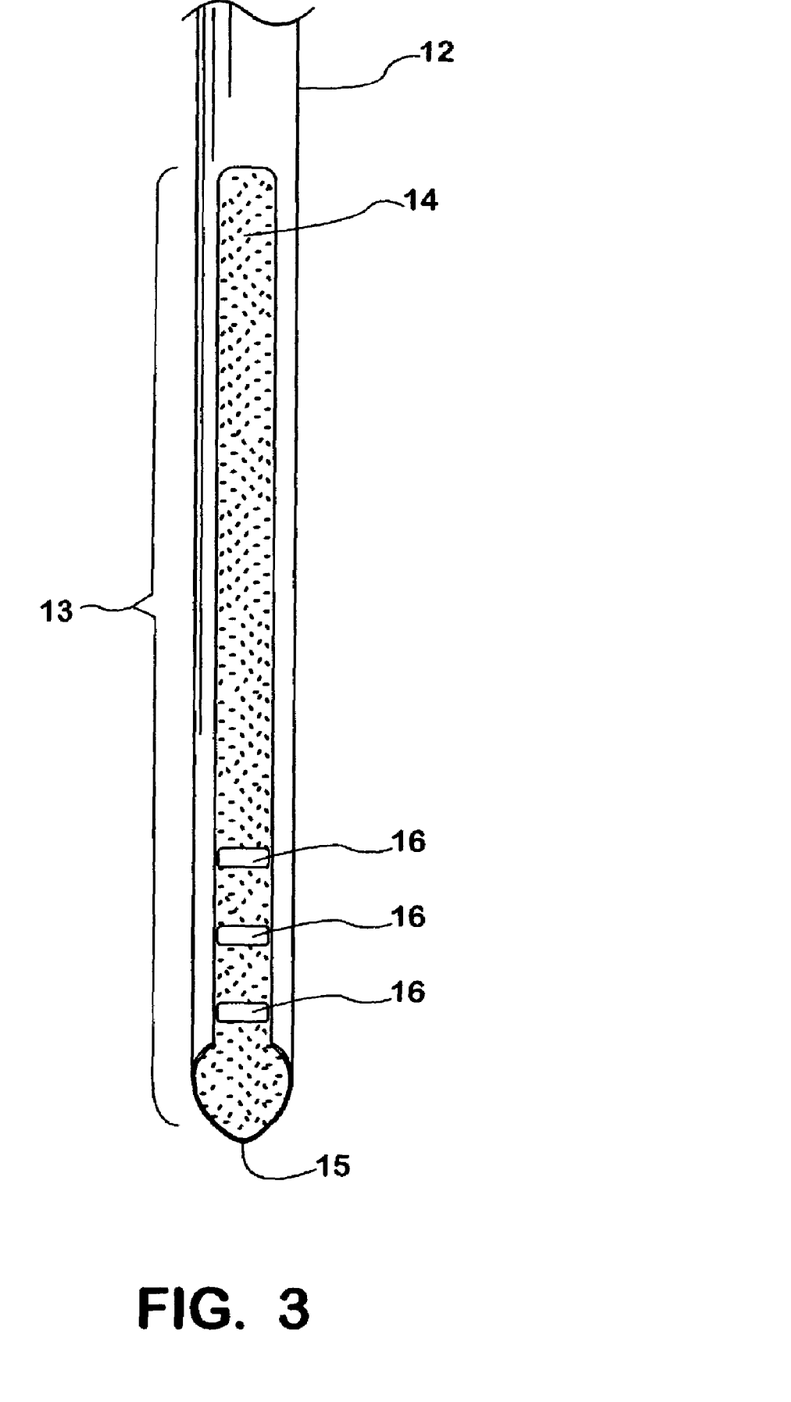
FIG. 3 is an enlarged frontal view of the distal trough portion of the sampling cannula according to one embodiment of the invention.

Referring to FIGS. 1, 2 and 3, the sampling cannula of the invention generally comprises a cannula body 10 structure having a longitudinal body with proximal and distal portions 11 and 12 respectively. The distal portion 12 of the sampling cannula comprises a trough portion 13 in which the cannula 10 structure is circumferentially incomplete, creating an exposed interior surface 14 of the sampling cannula viewable through an elongated open portion on the opposite side from an intact portion. The trough portion 13 originates at a location proximal to the distal tip and extends to terminate at the distal tip 15 of the cannula body 10. The sampling cannula, by way of the trough portion 13, is adapted to rotate about its longitudinal axis in order to sever a sample from the sampling site when positioned within an outer cannula 20 (see FIG. 4) which is structured to "core" into the bone tissue. The sampling cannula can be rotated 360° or less as needed to sever the sample from surrounding tissue. With the sample residing within the trough portion 13, the sampling cannula with the sample therein is withdrawn from the site. The wall opening(s) and friction-enhancing interior surface of the trough portion 13 facilitate retention of the sample. Accordingly, the amount of compressive force exerted upon the sample is significantly reduced during separation of the sample from surrounding tissue) and retaining the sample. Thus, damage to the sample and altering its in situ "architecture" as a result of compression is reduced or avoided.

The dimensions of the cannula 10 and trough 13 can vary according to the nature of the sampling site and/or desired sample size. The cannula cross-sectional diameter of the device can vary provided the device can effectively obtain and retain a sample within. For example, 8 gauge, 11 gauge or 13 gauge sizes can be used. For a given combination of dimensions and materials to be used, the hoop strength of the trough portion, i.e., structural integrity of the intact cross-sectional circumference of the intact portion of the cannula body, must be maintained to an extent sufficient to withstand the physical forces exerted upon it during the penetration and sampling stages of the bone marrow biopsy procedure.

The length of the trough portion 13 can vary according to the sample size desired provided the structural integrity of the device is not adversely compromised when sampling forces are exerted upon it. In a preferred embodiment, the trough portion 13 can have a length of up to about 4 cm. Most preferably, the length of the trough portion 13 is about 3 cm. A relatively long trough length is preferred so as to permit a lengthier core sample to be obtained from a patient. Such lengthy sample sizes allow the user to advantageously observe the pathological history of the sampled bone.

The distal tip 15 of the trough portion 13 of the sampling cannula 10 can be shaped to facilitate penetration and cutting of the bone tissue. In one embodiment and as shown in FIG. 2, the tip is angled relative to the longitudinal axis of the cannula and comprises a distal cutting edge which is beveled or shaped into a rounded curve as shown in FIGS. 1 and 3. In a preferred embodiment, the overall length of the sampling cannula is such that when positioned within the outer cannula, the distal cutting tip 15 of the sampling cannula resides within the outer cannula proximal to the distal tip of the outer cannula.

The dimensions of the trough portion 13 in terms of cross-sectional intact circumference of the cannula body 10 can vary provided sampling by rotational motion thereof can effectively sever and retain a sample therein without adversely compromising the structural integrity of the trough portion. In addition to trough portion length, the rigidity of the cannula body material, thickness of the cannula wall, diameter (gauge) of the cannula all must be balanced together with the amount of the intact portion of the cannula body in the trough. The amount of intact cross-sectional circumference of the trough portion can range from about 65% to about 85% of a complete cannula circumference. The amount of the intact portion of the trough will vary in cooperation with the diameter or size of the cannula used. Accordingly, the larger the diameter (or lower the gauge) of the cannula, the greater the amount of intact portion required. For example, if a 13 gauge cannula is used for the device, the amount of intact circumferential portion can be about 65%, whereas is an 8 gauge cannula is used, the amount of intact circumferential portion can be about 85%.

During sampling, opening(s) 16 through the wall of the trough portion function to permit a slight encroachment of the tissue therein, thereby physically "interlocking" or engaging a portion of the sample within and providing resistance to longitudinal migration of the sample. The number, size, shape and arrangement of wall opening(s) 16 in the trough portion 13 can vary provided the opening(s) 16 enhance the retention of the sample within the trough. In accordance with the invention, at least one opening 16 is present through the wall of the trough portion 13. In a preferred embodiment, a plurality of wall openings 16 in the trough portion 13 are present. In one embodiment shown in the Figures, three openings can be present.

The shape of the wall opening(s) 16 can vary as well. Opening shapes which can be used include, but are not limited to, rectangular, square, ovular, circular, triangular, and the like. A preferred opening shape is substantially rectangular opening wherein the longer dimension is perpendicular to the longitudinal axis of the sampling cannula body as shown in FIG. 3, illustrating a plurality of substantially rectangular openings.

The size of opening 16, i.e., opening dimensions, can vary provided it is large enough to permit encroachment of the collected tissue sample while small enough to avoid compromising the structural integrity of the trough portion. When a substantially rectangular opening shape is used, the opening(s) can have a length (relative to the longitudinal axis of the trough portion) ranging from about 0.25 mm to about 0.75 mm. In one embodiment, a rectangular opening has a length of about 0.50 mm. The width (relative to the longitudinal axis of the trough portion) of a rectangular opening can vary as well. The depth (inward direction from a side view relative to the bottom-most portion of the base of the trough) can vary and is typically in the range from about 0.1 mm to about 0.3 mm.

When a plurality of openings are used, the trough portion of the device can comprise combinations of opening shapes having the different sizes, shapes, or both. According to the invention and when a plurality of openings are used, the arrangement of openings 16 in the trough portion 13 can vary as well. Suitable opening arrangements include, but are not limited to, linear alignment along the longitudinal axis of the cannula (as shown in the Figures) and staggered within the trough portion. In a preferred embodiment, a plurality of openings 16 are located within a distance from about 1 cm to about 1.5 cm from the distal end 15 of the trough portion 13.

Referring again to FIG. 3 and in another embodiment of the invention, the interior surface 14 of the trough portion 13 can further comprise a friction-enhancing surface texture that is adapted to facilitate sample retention. Surface textures which can be used include, but are not limited to, roughened surface textures. When roughened surface texture is used, the surface is roughened to the extent sufficient to increase coefficient of friction of surface to retain sample while at the same time not affording significant resistance to the movement of the tissue into the trough. Various techniques readily available to those skilled in the medical device arts can be used to roughen the interior surface of the trough portion, such as sandblasting and chemical etching. Some or all of the interior surface of the trough portion of the device can be textured.

Figure 4:
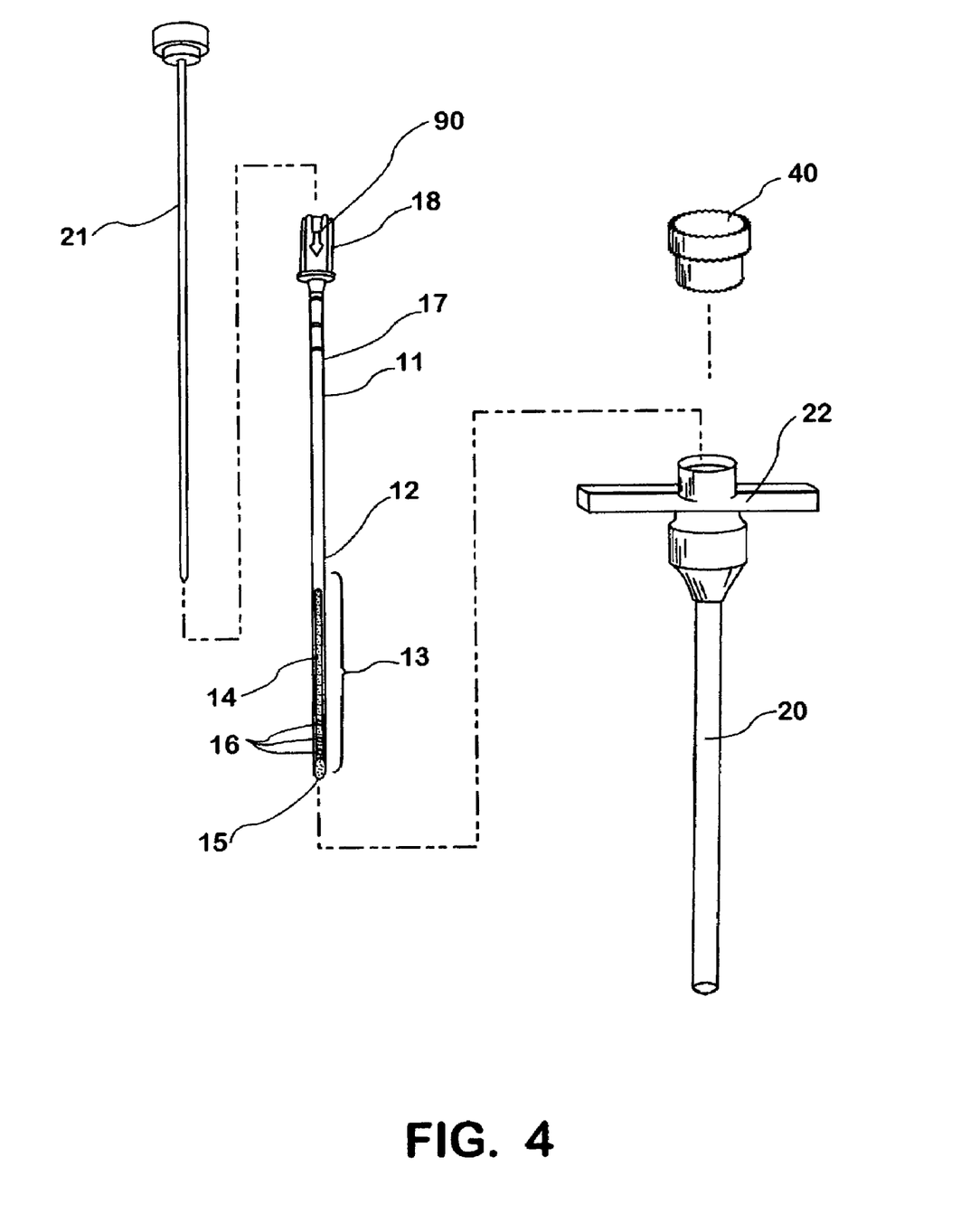
FIG. 4 is a disassembled view of a bone marrow biopsy system comprising a sampling cannula, outer cannula and stylet according to one embodiment of the invention.

In a further embodiment, the exterior surface of the proximal portion 11 of the sampling cannula can comprise viewable markings or indicia 17. Markings 17 which can be used include, but are not limited to, orientation indicia, depth markings, numbers, symbols, letters, and the like. Such markings can be printed, etched or embossed. In one particular embodiment and as shown in FIGS. 1, 2 and 4, the proximal portion 111 of the device comprises external depth markings 17. The markings are viewable upon displacement of the sampling cannula in the proximal direction while the remaining sampling cannula resides within the outer cannula.

Thus, in use, the distance of displacement of the sampling cannula relative to the outer cannula after the outer cannula has been advanced into the sampling site should substantially correspond to the length of the sample which will be obtained when the sampling cannula is likewise advanced and rotated to sever the sample.

The proximal portion 11 of the sampling cannula of the invention can further comprise a hub 18 coupled thereto in order to facilitate grip and handling by the user during operation of device, e.g., forward pressure for insertion in longitudinal direction and rotational motion for severing sample from site. The hub 18 can be attached to the cannula body 10 using a variety of conventional techniques, such as UV-curable adhesive bonding. The exterior surface of the hub 18 can comprise a surface texture, treatment or geometry to further facilitate grip and handling. The hub 18 can also further comprise markings or indicia, such as an orientation marking 90 (see FIGS. 1 and 4) indicating the position or alignment of the opening of the trough portion of the sampling cannula.

According to the invention, the sampling cannula can be used as a component of a bone biopsy assembly such as that described by Krueger et al., U.S. Pat. No. 6,443,910, the entire text of which is incorporated herein by reference. In general, bone biopsy assemblies that can be used which include the sampling cannula of the invention include those such as that shown in FIG. 4, which comprises an outer cannula 20 secured or affixed to a handle 22, and a stylet 21 structured to be removably inserted into the outer cannula 20 and which, when inserted into the outer cannula 20 is used to penetrate the cortex of the bone. The outer cannula 20 can be a component of an assembly having a handle 22 secured to the proximal region thereof, and can further comprise a cap 40 which can be positioned over the proximal end of the outer cannula 20 and handle 22 to prevent proximal movement of the stylet 21 during the penetration stage of the procedure.

Figure 5:
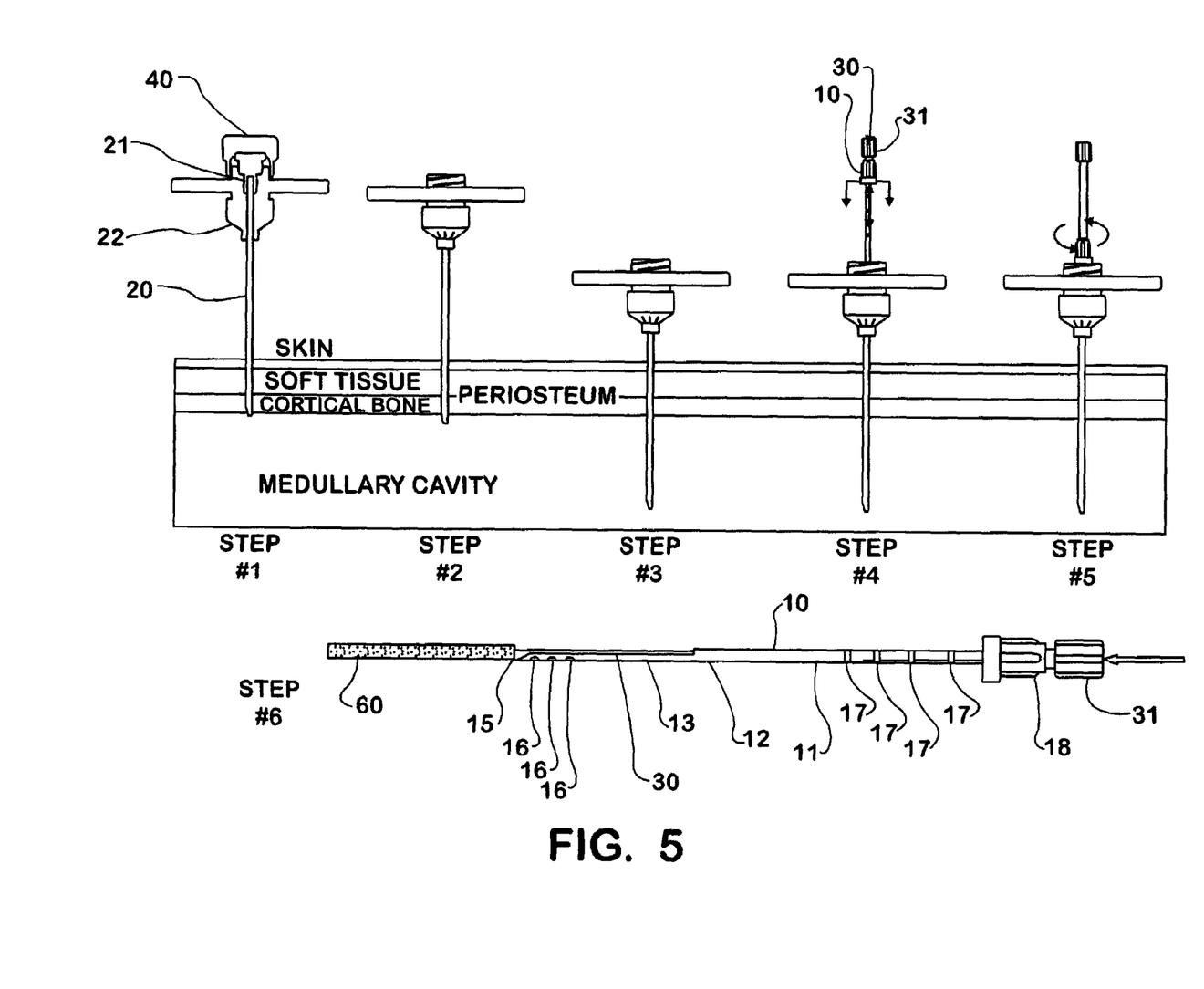
FIG. 5 is an illustration of a sequence of biopsy steps with a bone biopsy system comprising the sampling cannula according to one embodiment of the invention.

Accordingly, the handle 22 is fixed to the outer cannula 20, and the stylet 21 is positioned within the outer cannula 20 and the cap 40 secured onto the handle 22 and covering the proximal end of the stylet 30. The assembled system is then inserted into the bone as illustrated in FIG. 5. When the distal portion of the outer cannula 20 is positioned near the sampling site, the cap 40 is removed and the stylet 21 is withdrawn from the outer cannula 20. The outer cannula 20 is further advanced into the bone to "core" a sample in the longitudinal direction. Subsequently, the sampling cannula of the invention can is inserted into the outer cannula 20 until the distal end of the sampling cannula is positioned just proximal to the distal tip of the outer cannula 20, and then rotated to circumscribe and thus sever the sample from the surrounding tissue. The sampling cannula with the core sample 60 residing within the trough portion 13 is subsequently withdrawn.

The bone biopsy system can further comprise an ejector rod 30 adapted or structured to be inserted within the sampling cannula in order to expel the core sample from the sampling cannula. The ejector rod 30 can comprise an ejector rod hub 31. The ejector rod can be composed of any rigid or semi-rigid material suitable for such use, including polymeric and metallic materials. Preferably, the ejector rod 30 is composed of plastic.

The sampling cannula 10, outer cannula 20 and stylet 21 can be composed of any material which is sterilizable and suitable for use in medical devices and which can withstand the physical forces exerted upon it during bone biopsy techniques. Suitable materials include metals and metallic alloys, such as stainless steel and titanium. The hub, handle and ejector rod components can be composed of polymeric materials or plastic, and made according to conventional molding techniques readily available to those in the medical device field.

Process of Making the Device:

The following is one example of a manufacturing technique which can be used to make the device in accordance with one embodiment of the invention.

Raw stainless steel tubing is cut to the desired length using a disc cutter to prepare a cannula. A bevel or curved tip is created in one end of the cannula using a grinder at the desired angle relative to the longitudinal axis of the cannula. One or more of the cannulas are fixed onto a plate. A wheel grinder is applied to the uppermost surface of each cannula and applied to the desired depth to remove the uppermost surface of the cannula as well as the desired length of the cannula to be removed. The grinder thus creates a trough structure and exposes the interior of the cannula. Next, a grinding machine is applied to the underside intact portion of the cannula using one or more discs sized and spaced to create the desired dimensions of the openings in the trough portion. More than one opening can be created simultaneously. Electropolishing techniques using electrolytic acid solution can be used to remove burrs and particulate matter from the surface. The exposed interior of the trough portion of the cannula can be sandblasted to create the roughened surface texture. Additionally, the exterior surface of the proximal end of the cannula can be sandblasted as well to facilitate the bonding of a hub thereto. To attach a hub to the proximal end of the cannula, the hub can be positioned on the proximal end and bonding material can be injected into the space between.

Plastic components, for example a sampling cannula hub 18, can be formed in accordance with conventional molding equipment and methods readily available in the art.

Biopsy Procedure Using the Device:

Referring to FIG. 4, the following is an example of a bone marrow biopsy procedure using the device according to one embodiment of the invention.

The patient is prepared in accordance with standard surgical preparation techniques for bone biopsy procedures. As seen in Step #1, a bone biopsy assembly including an outer cannula 20 with a removable stylet 21 within and coupled to a handle 22 is inserted into the patient penetrating the skin and cortical layer of the bone to be sampled. Once the cortex of the bone has been penetrated by the distal end of the outer cannula 20, the stylet 21 is then removed as depicted in Step #2. As shown in Step #3, once the stylet has been removed, the outer cannula 20 is further advanced into the sampling site to create a "core" sample within the outer cannula. At this point, the device of the invention is inserted into the interior of the outer cannula to the desired depth as indicated by observing the proximal portion of the device outside the patient's body as depicted in Step #4. Once the device of the invention, specifically the trough portion of the device, has been advanced to the desired extent, the user rotates the hub as shown in Step #5 to rotate the trough portion of the device to sever the sample from the site. The device of the invention is then removed from the bone with the sample contained within the trough. Once outside of the patient's body, the ejector rod 30 can be inserted into the device in a longitudinal direction to expel the sample from the device as shown in Step #6. Alternatively and as shown in Steps #4 and 5, the ejector rod 30 can accompany the device of the invention throughout the insertion and removal of the device wherein the rod does not penetrate beyond the cortex.

INDUSTRIAL APPLICABILITY

The invention is useful in the medical field under circumstances where sampling a patient's bone tissue is needed. The device affords the practitioner or user the advantages of maintaining the architectural integrity of the sample as well as improved sample retention upon removal.

The invention has been described with reference to various and specific embodiments and techniques. It will be understood, however, that reasonable modifications and variations of such embodiments and techniques can be made without departing from the spirit or scope of the invention defined by the claims set forth below.

What is claimed is:

1. A bone marrow biopsy system comprising:
an outer cannula having a sharpened distal tip;
a sampling cannula having a distal trough portion in which the interior surface of said sampling cannula is exposed;
a plurality of wall openings located within said trough portion located proximal to the distal tip of said sampling cannula;
a friction-enhancing surface texture on at least a portion of the interior surface of said trough portion;
wherein said sampling cannula is adapted to be inserted into said outer cannula and to sever a sample from the sampling site by rotational motion of the sampling cannula; and
a stylet structured to be removably inserted into said outer cannula.

2. The bone marrow biopsy system according to claim 1 wherein the distal tip of the trough portion of the sampling cannula resides within the outer cannula such that the trough portion distal tip terminates proximal to the distal tip of the outer cannula.

3. The bone marrow biopsy system according to claim 1 further comprising an ejector rod.

4. The bone marrow biopsy system according to claim 3 wherein said ejector rod is composed of plastic.

5. The bone marrow biopsy system according to claim 1 wherein the sampling cannula trough portion comprises three wall openings.

6. The bone marrow biopsy system according to claim 1 wherein the sampling cannula wall openings have a generally rectangular shape, the longer sides of the rectangle being substantially perpendicular to the longitudinal axis of the sampling cannula.

7. The bone marrow biopsy system according to claim 1 wherein the sampling cannula further comprises markings located on the exterior surface of the proximal portion of the sampling cannula.

8. The bone marrow biopsy system according to claim 7 wherein the sampling cannula markings comprise sampling depth indicia that are viewable upon displacement of the sampling cannula in the proximal direction relative to the outer cannula.

9. The bone marrow biopsy system according to claim 1 wherein the proximal portion of said sampling cannula further comprises a hub.

10. The bone marrow biopsy system according to claim 9 wherein the sampling cannula hub further comprises orientation indicia relative to the trough portion.

11. A bone marrow biopsy system comprising:
a sampling cannula having a distal trough portion in which the interior surface of said sampling cannula is exposed;
a plurality of wall openings located within said trough portion located proximal to the distal tip of said sampling cannula;
a friction-enhancing surface texture on at least a portion of the interior surface of said trough portion;
wherein said sampling cannula is adapted to sever a sample from the sampling site by rotational motion of the sampling cannula; and
an ejector rod structured for removable insertion into said sampling cannula to expel a sample residing therein.

12. The bone marrow biopsy system according to claim 11 wherein the proximal portion of said sampling cannula comprises depth indicia that are viewable upon displacement of the sampling cannula in the proximal direction relative to the outer cannula.

13. The bone marrow biopsy system according to claim 11 wherein the proximal end of said sampling cannula comprises a hub.

14. The bone marrow biopsy system according to claim 13 wherein the hub further comprises orientation indicia relative to the trough portion.

* * * * *